(12) United States Patent
Landauer (10) Patent No.: US 6,256,896 B1
(45) Date of Patent: Jul. 10, 2001

(54) INFANTOMETER FOR MEASURING HEIGHT OF INFANTS

(75) Inventor: Konrad S. Landauer, Chicago, IL (US)

(73) Assignee: Clover Global Group. Inc., Chicago, IL (US)

( * ) Notice: Subject to any disclaimer, the term of this patent is extended or adjusted under 35 U.S.C. 154(b) by 0 days.

(21) Appl. No.: 09/399,029

(22) Filed: Sep. 21, 1999

Related U.S. Application Data (63) Continuation-in-part of application No. 08/967,809, filed on Nov. 12, 1997, now Pat. No. 5,974,678.

(51) Int. Cl.[7] .............................. G01G 19/50; G01B 5/02
(52) U.S. Cl. ................................ 33/512; 33/806; 33/515; 177/245
(58) Field of Search ............................. 33/512, 783, 806, 33/809, 810, 511, 515, 760; 177/245

(56) References Cited

U.S. PATENT DOCUMENTS

| | | | |
|---|---|---|---|
| 1,555,792 | * 9/1925 | Souder | 33/810 |
| 3,492,737 | * 2/1970 | Swanson | 33/809 |
| 3,667,561 | * 6/1972 | Hutchinson et al. | 177/245 |
| 4,939,849 | * 7/1990 | Johnson | 33/512 |
| 5,097,617 | * 3/1992 | Craven | 33/511 |
| 5,499,457 | * 3/1996 | Weiler et al. | 33/512 |
| 5,637,838 | * 6/1997 | Arey et al. | 177/245 |
| 5,974,678 | * 11/1999 | Landauer | 33/512 |

OTHER PUBLICATIONS

Tanita Pediatric Scale—Model BLB–12 (Date Unknown) Tanita Corporation of America, Arlington Heights, Illinois.

* cited by examiner

*Primary Examiner*—Christopher W. Fulton
(74) *Attorney, Agent, or Firm*—Milton S. Gerstein (57) ABSTRACT

An infantometer in combination with a pediatric weighing scale. The infantometer has a pediatric-scale mounting means projecting downwardly from the main frame thereof with releasable retaining means for releasably retaining the infantometer to a pediatric scale, where the infant-receiving tray of the infantometer also serves as the infant-receiving tray of the pediatric weighing scale, whereby both height and weight measurements of an infant may be carried out substantially simultaneously.

5 Claims, 6 Drawing Sheets

INFANTOMETER FOR MEASURING HEIGHT OF INFANTS

CROSS REFERENCE TO RELATED APPLICATION

The present application is a continuation-in-part of commonly-owned application Ser. No. 08/967,809, filed on Nov. 12, 1997 now U.S. Pat. No. 5,974,678.

BACKGROUND OF THE INVENTION

The present invention is directed to a mechanical device for measuring the height of infants up to thirty-seven inches, which is typically the height of a two-year old. It is, in some cases, extremely critical to be able to measure the height of an infant accurately, with very little margin of error tolerated, for those infants requiring the periodic administering of human growth hormone, or HGH. The amount of dosage of HGH, as well as the change in any dosage, is dependent upon the measured height of the infant initially, and the differential growth rates thereafter. By being able to obtain a substantially exact measurement of the height of the infant, the dosage to be administered may be more fine-tuned, thus preventing over-dosaging or under-dosaging, either of which may have potentially adverse effects on the infant. A measurement that is off by one-quarter inch can affect the determination of the amount of HGH to be administered.

There are presently used mechanical infantometers that are used to measure the infant's height. However, they suffer from a number of drawbacks and disadvantages. A first type sold by Seca Corp. is made of vinyl or rubber which is unfolded during use. There is a measuring scale imprinted on the face of the unit, with upstanding head and foot plates being used to provide the reading. The problem with this infantometer is that it requires two persons, one to hold the infant still, and the other to do the actual measuring. In addition, this type of infantometer must be unfolded and stretched out, and, since it is made of vinyl or rubber, any stretching thereof will distort the measurement, since the imprinted indicia lines of the scale on the face of the unit will be stretched greater or closer apart depending upon how much the unit is stretched. This will, therefore, invariably result in a less exact reading. Moreover, the stretching of the unit will sometimes cause the edges thereof to curl, also resulting in a skewed reading. Moreover, the infant often tends to stick to the rubber or vinyl, making it difficult to position and reposition the infant as necessary.

In a second type of infantometer also sold by Seca Corp., instead of rubber or vinyl being used, wood is used instead. In this type, the infantometer does not require unfolding, and has scales on the edges thereof, with one sliding foot-plate being moved to indicate the indicia indicative of the height of the infant. There is also provided a fixed head-plate against which the infant's head is placed. This type also suffers from the disadvantage of requiring two persons, one to hold the baby to ensure he or she does not fall off, and a second to do the actual measuring. Moreover, another drawback of this type of infantometer is that it is ofttimes difficult or cumbersome to slide the sliding foot-plate to indicate the measurement, since the part that mounts the foot-plate to the wooden base also serves as a support that helps to support the infantometer on a flat surface; thus, when sliding the foot-plate, both static and dynamic friction must be overcome, which, by itself, can lead to an errant measurement.

SUMMARY OF THE INVENTION

It is, therefore, the primary objective of the present invention to provide a mechanical infantometer that overcomes all of the disadvantages and drawbacks of the prior-art mechanical infantometers.

It is a primary objective of the present invention to provide an infantometer that safely supports an infant thereon without the need of a person holding the baby, whereby only one person is needed to use the infantometer of the invention, in contradistinction to the prior-art infantometers that require two persons.

It is another primary objective of the present invention to provide an improved mechanical infantometer that provides a more exact measurement of the height of an infant by reducing friction of sliding parts.

It is another primary objective of the present invention to provide an improved mechanical infantometer that allows for a quicker measurement of the height of an infant.

It is yet another objective of the present invention to combine the infantometer of the invention with an infant weighing scale, whereby there is provided a combination of a height and weight measurement apparatus.

Toward these and other ends, the infantometer, in the preferred embodiment of the present invention, is made of styrene, and has two telescoping halves, with each having measuring indicia thereon. The first stationary half has a fixed head-plate against which the head of the infant is placed. The measuring indicia or scale on the first half is located along one side edge thereof. The second, sliding half telescopingly slides in the first fixed half, and has a fixed foot-plate attached at it distal, free end for abutment against the feet of the outstretched infant. The measuring indicia or scale on the second half is located along a side edge thereof laterally opposite to that corresponding to the first half. The two halves have an upper surface that form a trough or concave central section on which the infant is supported, whereby the infant is prevented from escaping or falling out. The bottom surface of both halves may also define curved side edges to reduce frictional surface-to-surface contact, which friction is further reduced owing to the fact that the infantometer is made of low-coefficient-of-friction styrene.

In a second embodiment, there is provided a main frame formed as a trough or concave section, having at a first end thereof a fixed handle-portion, and having adjacent the second end thereof, a slidable-mounted handle-portion that is slidable along the main frame. The main frame has a measuring scale alone one side edge. The placement of the second slidable handle-portion indicates on the scale the height-measurement of the infant.

In a modification, the second embodiment is combined with an infant-weighing scale, whereby the main frame of the infantometer serves as both the means for measuring the height of the infant, and also serves as the weighing scale's receptacle for receiving and retaining the infant for weighing.

BRIEF DESCRIPTION OF THE DRAWINGS

The invention will be more readily understood with reference to the accompanying drawing, wherein.

DETAILED DESCRIPTION OF THE INVENTION

Referring now to the drawings in greater detail, and to FIGS. 1–7 for now, there is shown the preferred embodiment 10 of the infantometer of the invention. The infantometer 10 is made up of two relatively sliding halves or parts 12, 14, each being preferably made of a low friction thermoplastic such as styrene. The first half or part 12 telescopingly receives therein the second half or part 14. Each half 12, 14 is provided with half of a linear ruler or scale. The first half has a lower scale-half 12' running from between 1 and 17 inches. The scale-half 12' is located along one lateral side edge 16. The second half has an upper, second scale-half 14' running from between 37 and 17 inches. The upper, second scale-half 14' is located along one lateral side edge 18, parallel to but laterally opposite relative to the side edge 16 containing the first scale-half. The first scale-half 12' extends normally and in ascending order of magnitude, with the greatest value, such as 17 inches, being located at the transverse edge-surface 20 of the first half 12. In contrast, the upper, second scale-half 14' starts with its greatest value, such as 37 inches, at its transverse edge 22, and decreases in value in direction along lateral edge 14' away from the first part or half 12. This is so, so that when the tallest infant is being measured, the transverse edge-surface 20 of the first half 12 acts as an index to indicate the measurement. The reason why the first scale-portion goes up to 17 inches is that a new born is usually greater than 17 inches, and the reason why second half stops at 37 inches is that at that age two the baby can usually walk, and, therefore, may be measured by a standard statiometer.

Figure 1:
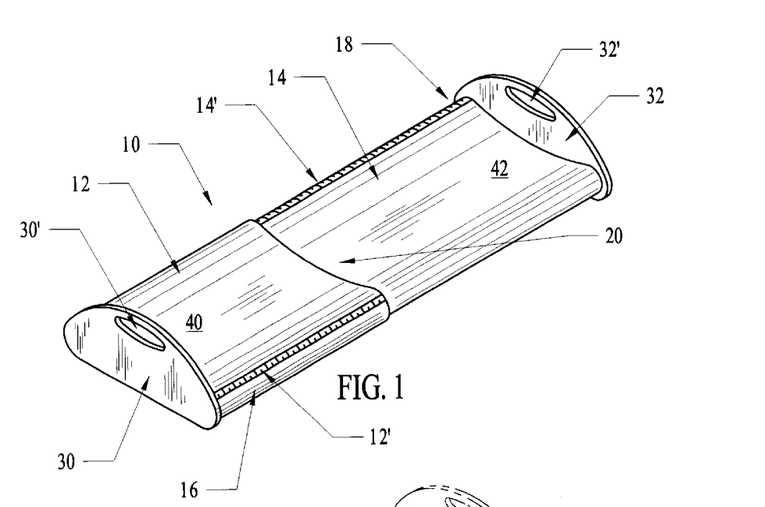
FIG. 1 is an isometric view of the infantometer of the invention.
Figures 2, 4:
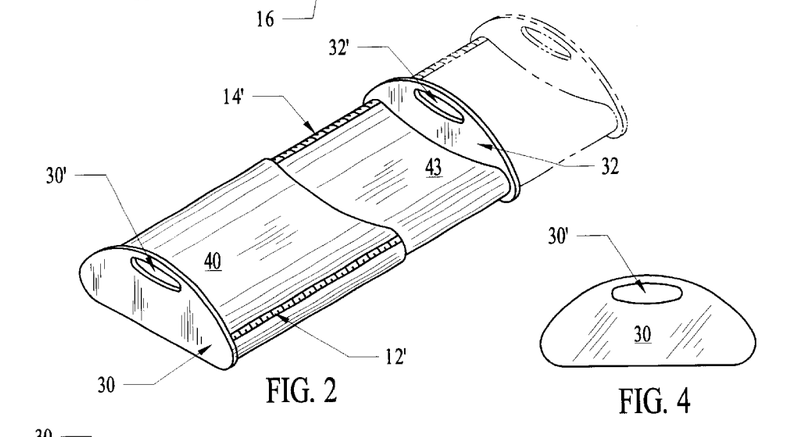
FIG. 2 is an isometric view of the infantometer showing the variable positioning thereof for measuring the height of an infant.
FIG. 4 is an end view thereof.
Figure 3:
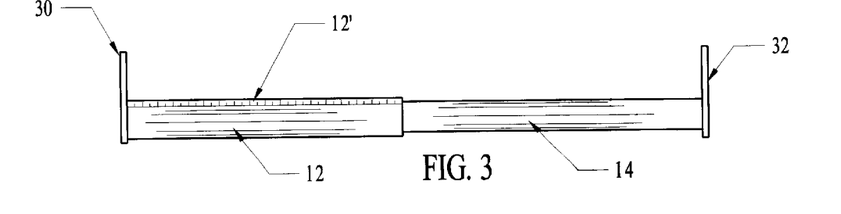
FIG. 3 is a side view thereof.
Figure 5:
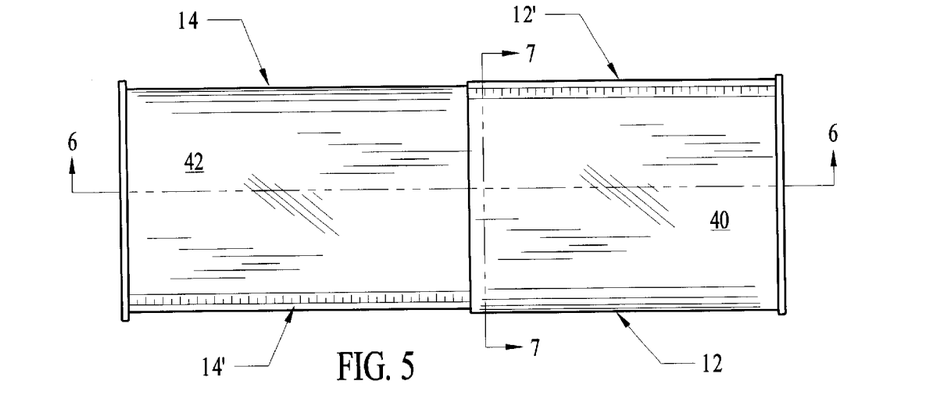
FIG. 5 is a top view thereof.
Figure 6:
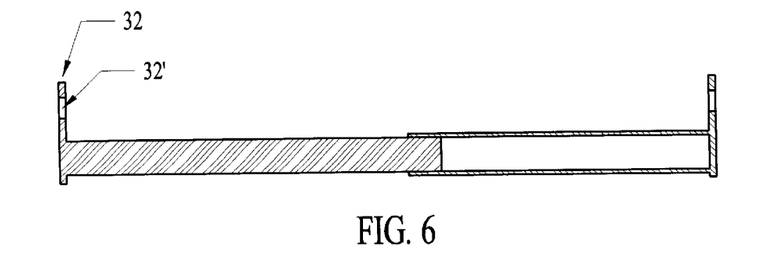
FIG. 6 is a cross-sectional view taken along line 6—6 of FIG. 5.
Figure 7A:
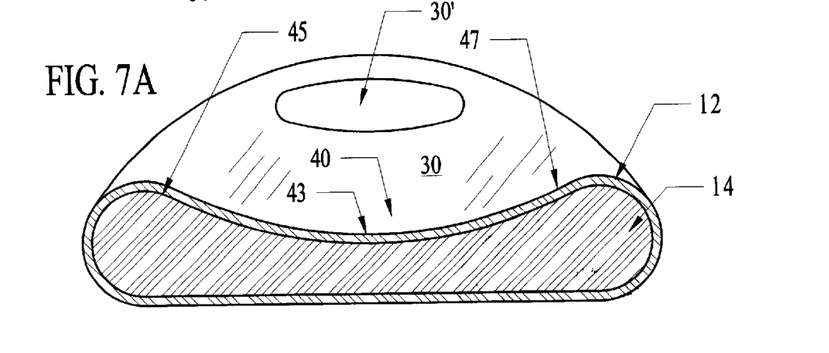
FIG. 7A is a cross-sectional view taken along line 7—7 of FIG. 5.

Each half or part 12, 14 has an upstanding handle 30, 32, respectively, with an opening 30', 32', respectively, for allowing a hand to grip the handle, in order to slidingly open or close the two sliding parts 12, 14, in order to measure an infant, and which allows the device to be opened up by just one person. The holes also allow the device to be carried easily. The handle 32 has a lower or bottom surface 34 that protrudes downwardly a slight amount below the bottom surface of the second half 14, as best seen in FIG. 6, which protrusion is approximately the same as the thickness of the lower or bottom surface 36 of the first part or half 12, so that the device 10 is supported on a support surface evenly. This considerably reduces the friction as the second part 14 is slid in or out. Also, the bottom of the handle 32 may be slightly concave-shaped so that only the lateral ends of the bottom surface of the handle 32 contacts the support surface therebelow. In addition, the bottom or lower surface of the first part or half 12 may be slightly concave, as seen in FIG. 7A, so that frictional contact with the supporting surface therebelow occurs along the central portion of the bottom or lower surface 36. Preferably, the bottom surface 36 has a straight middle section of between five and seven inches that contacts the supporting surface therebelow, with the bottom surface thereafter curving upwardly to form upwardly curved side walls, described hereinbelow.

Figure 7B:
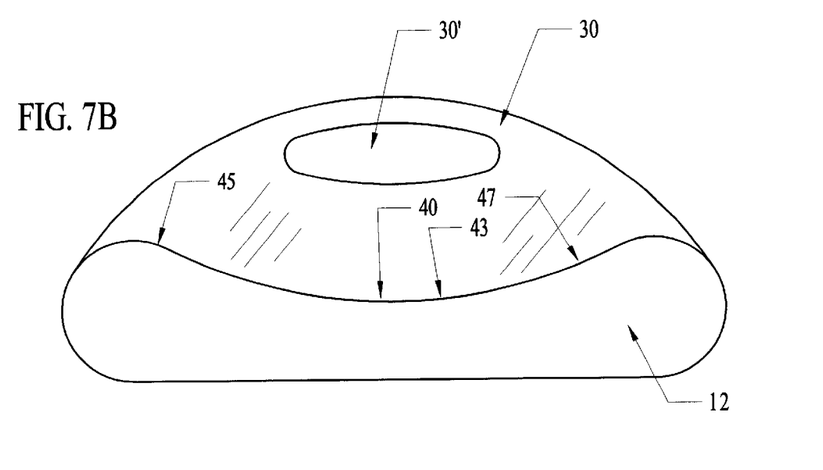
FIG. 7B is an end view of the first part of the infantometer showing the upper, concave supporting surface thereof.

The upper surface 40, 42 of the first and second halves 12, 14, respectively, is slightly concave-shaped or arcuate in order to prevent the infant from falling off. Thus, the measurement of the height of the infant may be performed by just one person, since there is no requirement of another person holding the infant down to prevent his or her falling off. In the preferred embodiment, as can be seen in FIGS. 7A and 7B, the upper surface 40 or 42 defines a concave-shaped surface that defines a top surface 43 with upwardly-inclined side walls 45, 47. Each side wall 45, 47 defines an initial section joined to the top surface 43; the initial sections, and therefore the width of the top surface 43, are spaced about eight inches apart, in the preferred embodiment, which is the minimum distance between the two shoulder blades of the smallest infant to be measured by the device 10. For larger infants, with shoulder blades spaced farther apart, higher elevations along the concave, curved side walls are used to support the shoulder blades. It is important that the shoulder blades are supported, and not the shoulders, in order to obtain an accurate reading by keeping the baby well-supported and stationary on the device via the support of the shoulder blades. In the preferred embodiment, the maximum height of each side wall, at the extreme edge, is about 2.2108 inches, while the overall width of device is 12.0117 inches. The infantometer 10 is used to measure infants up to 37 inches tall, which is about two years of age. The overall length of the device is about 38 inches.

Figure 8:
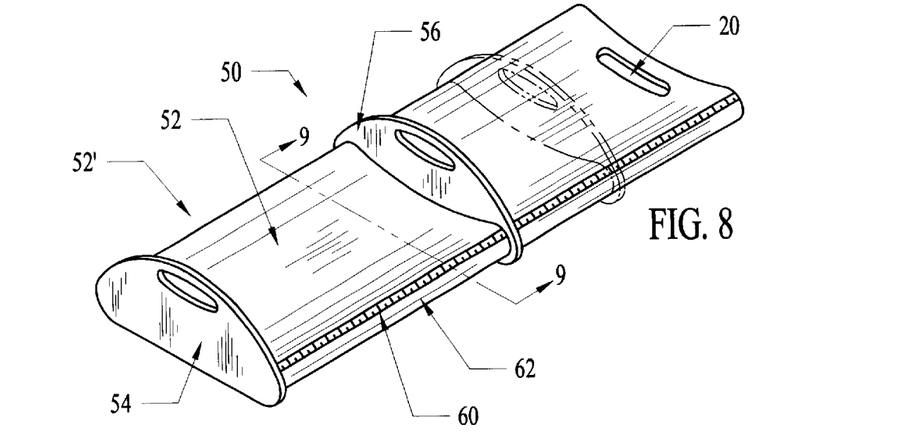
FIG. 8 is an isometric view of a second embodiment of the infantometer of the invention.
Figure 9:
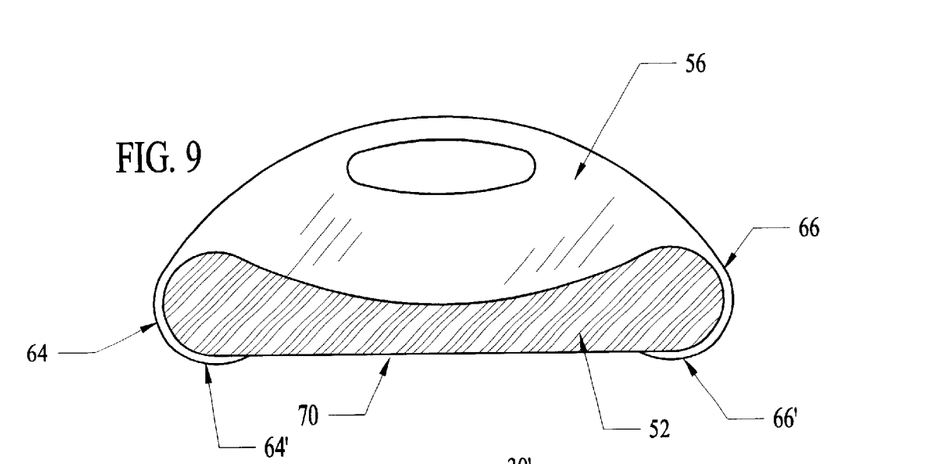
FIG. 9 is a cross-sectional view taken along line 9—9 of FIG. 8.

In FIGS. 8 and 9, there is shown a second embodiment 50 of the infantometer, also made preferably of styrene. In this embodiment, there are no sliding halves, but rather one main plate 52 having one fixed handle 54 at one end 52', and a slidable handle 56 that is movable along the main plate. The main plate has imprinted, or otherwise laid, a scale 60 running sequentially from 1 to 37 inches. The scale 60 is located along one lateral edge surface 62 of the main plate. The upper surface of the main plate 52 is concave like that of the two halves of the first embodiment, for the same reasons indicated there. The movable handle 56 defines arcuate end-regions 64, 66 that wrap around respective side edges of the main plate 52 for securing the handle thereto yet permitting sliding movement. These arcuate end-regions also define supports 64', 66' which support the handle, and, therefore, the main plate on a supporting surface, to thereby minimize surface contact therebetween, to thus reduce friction, whereby it is easier to move or slide the handle 56 for measuring the infant. The slidable handle 56 also has a convex-shaped lower surface 56" that is contoured to the concave-shape of the upper surface of the main plate 52. This convex-shaped lower surface 56" serves as an indicator on the scale 60 for reading the indicia of the scale for determining the height of the infant laid therealong. The stationary handle 54 may also have a downwardly protruding section below the lower or bottom surface 70 of the main plate approximately equal to the thickness of the supports 64', 66' similar to the handle on the movable half 14 of the first embodiment of FIG. 1. The movable handle 56 is also provided with an opening for receiving the hand for gripping thereby, in order to side the handle to the appropriate position for measuring. The main plate also has an opening 70 at one end thereof, remote from the end thereof that mounts the fixed handle 54, by which the infantometer 50 may be carried and transported.

Figure 10:
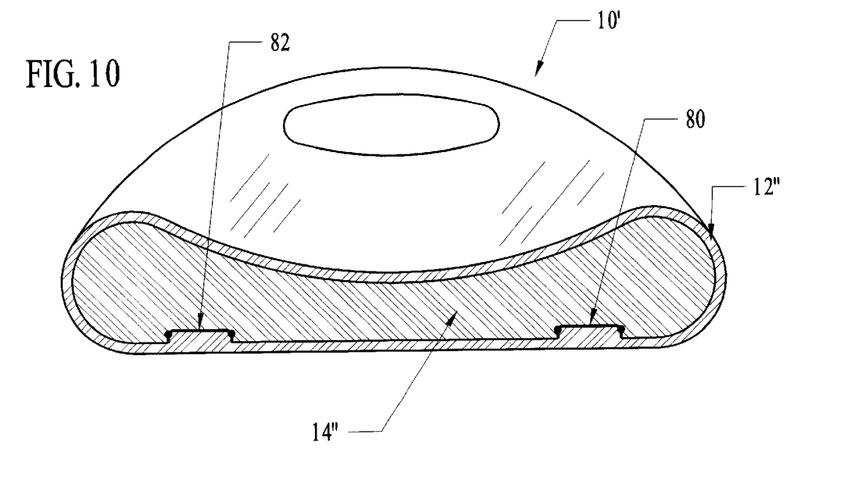
FIG. 10 is a cross-sectional view similar to FIG. 7 with the addition of ball bearings to aid in the reduction of friction.

Referring now to FIG. 10, there is shown a modification of the first embodiment. In this modification 10', the first stationary half or part 12" includes ball bearing mounts 80, 82 on each lateral side, by which the inner, slidable half or part 14" is mounted for basically friction-free movement.

Referring now to FIGS. 11–17, there is shown a modification of the second embodiment of FIG. 8. In this modification, the infantometer 50 is combined with a conventional infant or pediatric weighing scale 100. The infant's weighing scale is preferably a pediatric scale manufactured by Tanita Corp., model number BLB-12, with which scale there is associated a slidable, removably-mounted receiving tray or trough in which is placed the infant during weighing. This trough or tray has a pair of bottom runners or rails that slidably telescope over the perimetric rim of the pediatric scale's main housing. This rim has at least one notch formed along one of a pair of opposing parallel edge-surfaces against which the bottom runners of the trough abut as the trough is slid onto the perimetric rim of the pediatric scale. One bottom runner has a spring-biased detent lever that engages with a notch of the perimetric rim of the pediatric scale, in order to thereby firmly, yet removably, attach the receiving trough or tray to the pediatric scale. In order to remove the trough or tray from the scale 100, one merely depresses the spring-biased detent-lever, to release its engagement with the notch, and then one simply slides the tray off. The weight-sensing section of the pediatric scale 100 supports the perimetric rim by which the weight of the infant is gauged.

Figure 11:
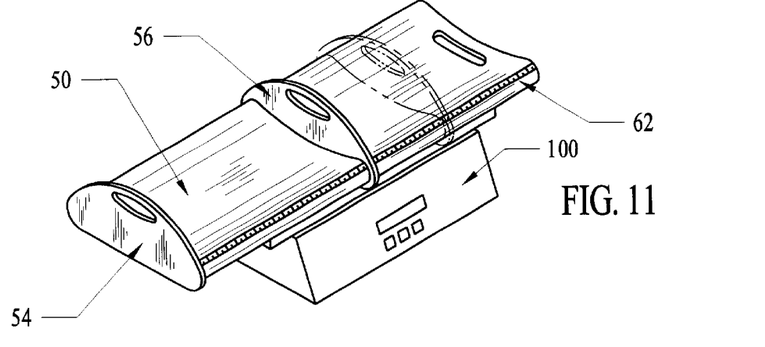
FIG. 11 is an isometric view of a modification of the infantometer of FIG. 8 showing the infantometer of the invention in combination with an infant's weighing scale, whereby the infantometer also serves as the receiving trough for the weighing scale.
Figure 12:
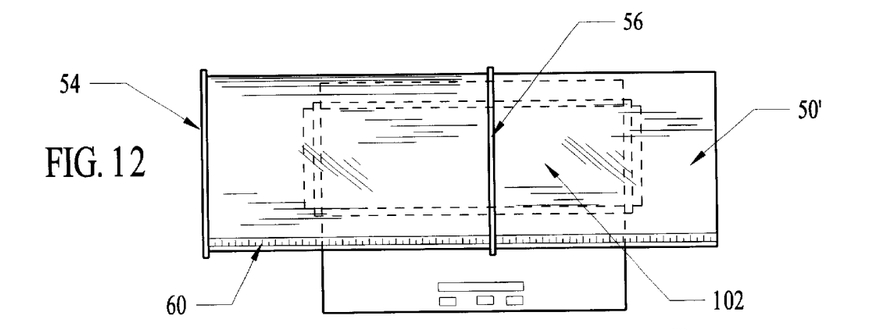
FIG. 12 is a top view thereof.
Figure 13:
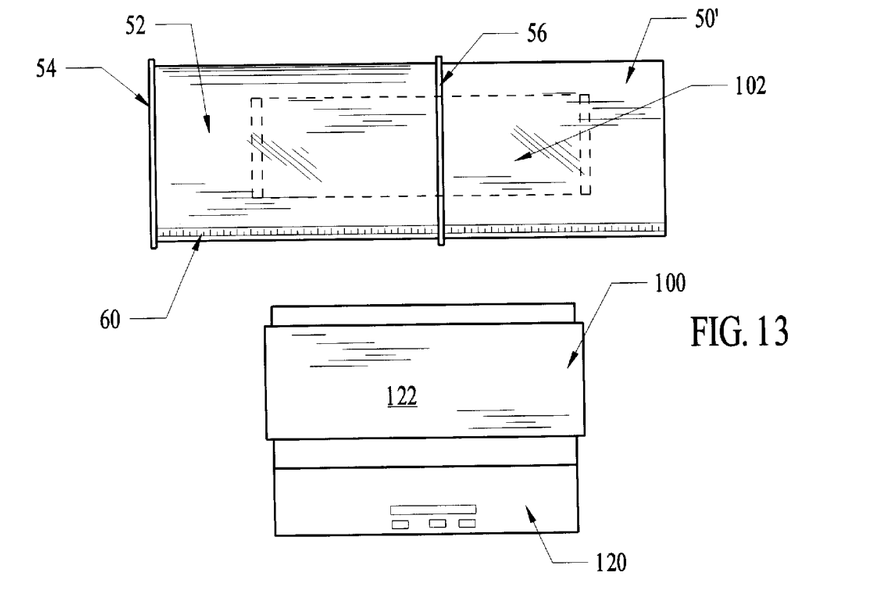
FIG. 13 is an assembly view showing the removable interconnection between the infantometer and the weighing scale.
Figures 14, 15, 16:
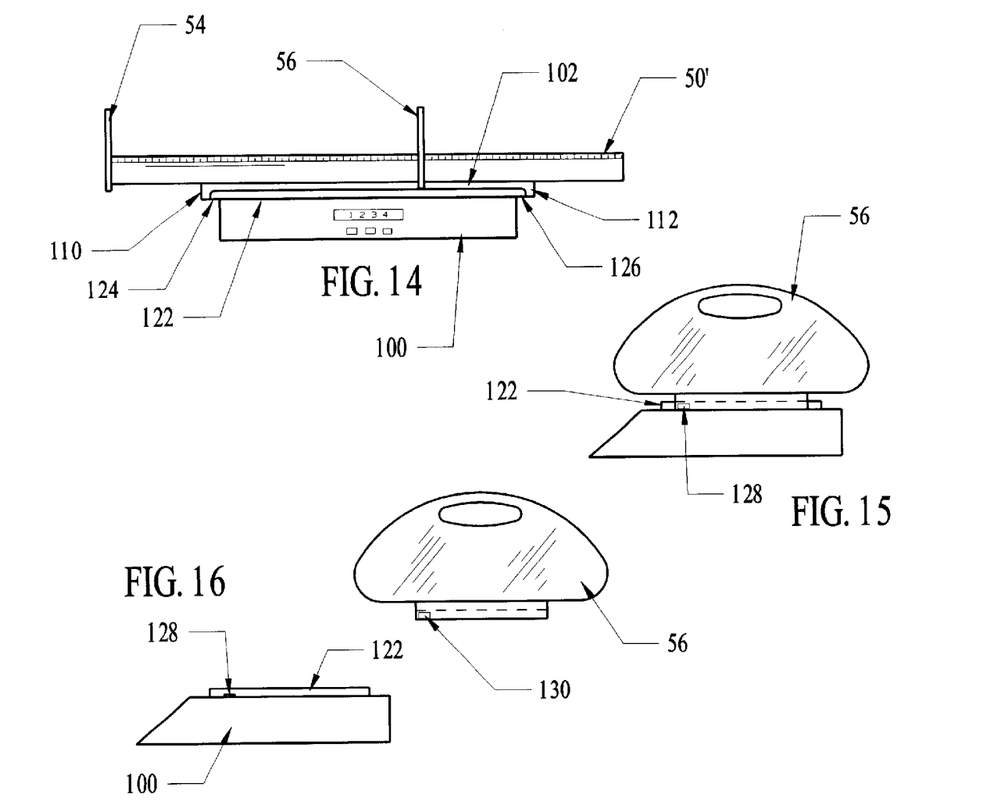
FIG. 14 is a front view of the combination infantometer and weighing scale of FIG. 11.
FIG. 15 is an end view thereof.
FIG. 16 is an end assembly view, showing the portable sliding interconnection between the infantometer and the weighing scale.
Figure 17:
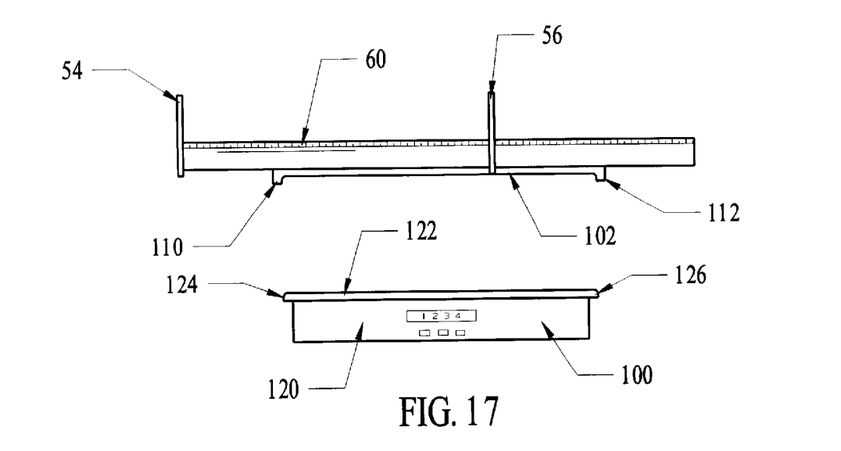
FIG. 17 is a front assembly end view, showing the portable interconnection between the infantometer and the weighing scale.

In the modification of FIG. 11, the infantometer 50' is provided with a downwardly-extending pediatric scale attaching portion 102, as best seen in FIGS. 14 and 17. The attaching portion 102 is affixed, or otherwise secured, to the bottom surface 104 of the infantometer 50'. The attaching portion 102 has a main portion 106 directly secured to the bottom surface 104 of the infantometer, and a pair of spaced-apart, downwardly-extending runners or rails 110, 112, which serves the same function as the runners of the conventional receiving trough or tray associated with the pediatric scale 100, as described above; that is, these runners 110, 112 serve to releasably and removably mount the infantometer to the upper perimetric rim of the pediatric scale 100, whereby the infantometer 50' not only serves as an infant's height-measuring device, but also serves as the receiving trough or tray for the pediatric scale 100. As can be seen in FIGS. 12, 13, 15 and 16, the width of the attaching portion 102 is less than the main frame 52, so that the handle 56 may be slid without obstruction along the side edge-surface 62. Also, preferably, the length of the attaching portion 102 is less than the length of the main frame 52.

As best seen in FIGS. 14–17, the pediatric weighing scale 100 is provided with a main housing 120 and an upper mounting section defining a projecting perimetric rim-portion 122. The rim 122 defines a pair of opposite, spaced-apart, parallel edge-surfaces 124, 126. One of the edge-surfaces 124, 126 is provided with at least one notch 128, and preferably a series of notches, in which spring-biased detent lever 130, formed in a corresponding one of the runners 10, 112, is received. The lever is identical to, and serves the same function as, the spring-biased detent lever provided in one of the runners of the conventional receiving trough or tray associated with the conventional pediatric scale, as described above.

As can be seen when viewing FIG. 16, the infantometer 50' is mounted to the pediatric scale by laterally sliding the runners 110, 112 along protruding edge-surfaces 124, 126 of the rim 122 of the upper portion of the main housing of the pediatric scale 100, until the spring-biased, pivotal detent-lever 130 engages the notch 128, whereupon the infantometer is secured to the pediatric scale. After such attachment, an infant is placed on the upper surface 52 of the infantometer, where he or she is measured for length via the sliding handle-portion 56, and for weight by means of the pediatric scale 100, with the infantometer serving the dual function of receiving and retaining the infant for both height and weight measurements. In order to remove the infantometer from the scale 100, one merely depresses the detent-lever 130, in the same manner that the detent-lever associated with the conventional trough or tray for use with the conventional pediatric scale is depressed, as described above.

In using the device, while the infant is being measured for height by the infantometer, substantially simultaneously therewith, the weight of the infant is measured by the pediatric scale.

While specific embodiments of the invention have been shown and described, it is to be understood that numerous changes and modifications may be made therein without departing from the scope, spirit and intent of the invention as set forth in the appended claims.

What I claim is:

1. An infantometer for measuring the height of an infant, comprising:

a main frame comprising a main body portions having an upper surface for safely receiving and retaining an infants and a first and second end;

scale means on said main body portion for indicating the height of an infant placed on said main body portion;

first handle means mounted to said main body portion at said first end; and second handle means movable relative to said first handle means for sliding movement toward and away from said first handle means along said main body portion in a direction between said first and second ends;

in combination with pediatric scale means for measuring the weight of an infant;

said main frame comprising a pediatric-scale mounting means for mounting the infantometer to said pediatric scale means;

said pediatric scale means comprising a main housing having an upper portion, said upper portion comprising a pair of spaced-apart, projecting parallel mounting elements;

at least one of said mounting elements rails having first cooperating means;

said pediatric-scale mounting means for mounting the infantometer to said pediatric scale means comprising a pair of spaced-apart, downwardly-projecting rails for releasable engagement with said spaced-apart, parallel mounting elements of said upper portion of said main housing of said pediatric scale means;

second cooperating means for cooperating with said first cooperating means for removably mounting said main body portion to said pediatric scale means, said second cooperating means being mounted to at least one of said pair of spaced-apart, projecting rails;

said first and second cooperating means releasably retaining said mounting means to said spaced-apart, projecting mounting elements of said upper portion of said main housing;

said pediatric-scale mounting means for mountinq the infantometer to said pediatric scale means projecting downwardly from said main frame.

2. The infantometer for measuring the height of an infant according to claim 1, wherein said pair of rails are slid along said spaced-apart, projecting parallel edge-surfaces of said upper portion of said main housing of said pediatric scale means until said first and second cooperating means engage.

3. The infantometer for measuring the height of an infant according to claim 1, wherein said first cooperating means comprising one of at least one notch and at least one biased lever, and said second cooperating means comprises the other of the at least one notch and at least one biased lever for engagement with said at least one notch;

said pediatric-scale mounting means having a width less than the width of said main body portion, whereby there is no interference presented to the movement of said second handle means.

4. A method measuring both the height and weight of an infant using the combination of an infantometer and a pediatric weighing scale, comprising:

(a) removing a weighing tray associated with the pediatric weighing scale;

(b) releasably securing the infantometer to said pediatric weighing scale at the same location and by the same means by which the weighing tray associated with the pediatric weighing scale was releasably secured;

(c) placing an infant on the upper surface of the infantometer;

(d) measuring the height of the infant by means of the infantometer;

(e) while the infant is still supported on the upper surface of the infantometer, measuring the weight of the infant by means of the pediatric weighing scale.

5. The method according to claim 4, wherein, said steps (d) and (e) are carried out substantially simultaneously.

* * * * *